(12) United States Patent
Egorov et al.

(10) Patent No.: US 8,419,659 B2
(45) Date of Patent: Apr. 16, 2013

(54) METHODS FOR ASSESSMENT OF IMPROVEMENTS IN PELVIC ORGAN CONDITIONS AFTER AN INTERVENTIONAL PROCEDURE

(75) Inventors: Vladmir Egorov, Princeton, NJ (US); Heather van Raalte, Princeton, NJ (US); Armen P. Sarvazyan, Lambertville, NJ (US)

(73) Assignee: Artann Laboratories, Trenton, NJ (US)

( * ) Notice: Subject to any disclaimer, the term of this patent is extended or adjusted under 35 U.S.C. 154(b) by 0 days.

(21) Appl. No.: 13/439,165

(22) Filed: Apr. 4, 2012

(65) Prior Publication Data

US 2012/0259247 A1 Oct. 11, 2012

Related U.S. Application Data

(62) Division of application No. 13/083,494, filed on Apr. 8, 2011, now Pat. No. 8,187,208.

(60) Provisional application No. 61/239,087, filed on Sep. 2, 2009.

(51) Int. Cl.
*A61B 5/117* (2006.01)
*A61B 5/103* (2006.01)

(52) U.S. Cl.
USPC .......................................................... 600/591

(58) Field of Classification Search .................. 600/587, 600/462, 591, 438, 471; 707/1; 606/228
See application file for complete search history.

(56) References Cited

U.S. PATENT DOCUMENTS

| | | | | |
|---|---|---|---|---|
| 4,947,851 A * | 8/1990 | Sarvazyan et al. | ............ | 600/438 |
| 5,115,808 A * | 5/1992 | Popovic et al. | ............... | 600/438 |
| 5,265,612 A * | 11/1993 | Sarvazyan et al. | ............ | 600/471 |
| 5,524,636 A * | 6/1996 | Sarvazyan et al. | ............ | 600/587 |
| 5,678,565 A * | 10/1997 | Sarvazyan | .................... | 600/587 |
| 5,706,815 A * | 1/1998 | Sarvazyan et al. | ............ | 600/438 |
| 5,785,663 A * | 7/1998 | Sarvazyan | .................... | 600/587 |
| 5,810,731 A * | 9/1998 | Sarvazyan et al. | ............ | 600/438 |
| 5,833,633 A * | 11/1998 | Sarvazyan | .................... | 600/587 |
| 5,836,894 A * | 11/1998 | Sarvazyan | .................... | 600/587 |
| 5,860,934 A * | 1/1999 | Sarvazyan | .................... | 600/587 |
| 5,922,018 A * | 7/1999 | Sarvazyan | .................... | 600/587 |
| 6,091,981 A * | 7/2000 | Cundari et al. | ............... | 600/407 |
| 6,142,959 A * | 11/2000 | Sarvazyan et al. | ............ | 600/587 |
| 6,468,231 B2 * | 10/2002 | Sarvazyan et al. | ............ | 600/587 |
| 6,569,108 B2 * | 5/2003 | Sarvazyan et al. | ............ | 600/587 |
| 6,595,933 B2 * | 7/2003 | Sarvazyan et al. | ............ | 600/587 |
| 6,620,115 B2 * | 9/2003 | Sarvazyan et al. | ............ | 600/587 |
| 2007/0167819 A1 * | 7/2007 | Osborn et al. | ................ | 600/462 |
| 2008/0077053 A1 * | 3/2008 | Epstein et al. | ................ | 600/591 |
| 2010/0087756 A1 * | 4/2010 | Egorov et al. | ................. | 600/587 |
| 2010/0087856 A1 * | 4/2010 | Park et al. | ..................... | 606/228 |

* cited by examiner

*Primary Examiner* — Brian Szmal
(74) *Attorney, Agent, or Firm* — Boris Leschinsky

(57) ABSTRACT

Methods for assessment of pelvic floor conditions based on tactile imaging are described. The vaginal wall is deformed before and after an interventional procedure using a transvaginal probe equipped with tactile pressure sensors and a motion tracking sensor. The vaginal wall coordinates and pressure patterns are obtained during the examination and used to build 3-D tactile image of the vagina and to calculate elasticity modulus profiles and spacing profiles along selected lines inside 3-D tactile image. The "before" and "after" profile values at specified locations are then compared to each other and to thresholds or profiles for normal conditions of vagina and its support structures. Methods of the invention may be used in estimating an improvement after an interventional procedure such as pelvic tissue regeneration, muscle repair or implantation of a supporting structure.

5 Claims, 8 Drawing Sheets

METHODS FOR ASSESSMENT OF IMPROVEMENTS IN PELVIC ORGAN CONDITIONS AFTER AN INTERVENTIONAL PROCEDURE

CROSS-REFERENCE DATA

This application is a divisional of U.S. patent application Ser. No. 13/083,494 filed 8 Apr. 2011 entitled "Methods for assessment of pelvic organ conditions affecting the vagina", which in turn is a continuation-in-part of U.S. patent application Ser. No. 12/874,583 filed 2 Sep. 2010 entitled "Methods for characterizing vaginal tissue elasticity", now U.S. Pat. No. 8,052,622, which in turn claims a priority benefit from a U.S. Provisional Patent Application No. 61/239,087 filed 2 Sep. 2009 entitled "Methods of using a vaginal tactile imager for pelvic organ prolapse characterization, including that after a reconstructive surgery", all of which are incorporated herein in their respective entireties by reference.

REFERENCE TO GOVERNMENT-SPONSORED RESEARCH

This invention was made with the U.S. government support under SBIR grant No. AG034714 entitled "Vaginal Tactile Imager for Pelvic Floor Biomechanical Assessment" and awarded by the National Institute of Health, National Institute on Aging. The government has certain rights in this invention.

FIELD OF THE INVENTION

The present invention generally relates to methods for characterization of pelvic floor organs and support tissues. More specifically, the invention describes methods for assessment of pelvic organ conditions affecting the vagina such as pelvic organ prolapse, childbirth trauma and reconstructive surgery in women.

BACKGROUND OF THE INVENTION

Pelvic organ prolapse (POP) is the descent of the apex of the vagina, including the cervix (or vaginal vault after hysterectomy), anterior vaginal wall, and/or posterior vaginal wall. As prolapse progresses, pelvic organs may become displaced and even protrude outside the vaginal canal. POP is a highly prevalent condition affecting at least 50% of women in the US during their lifetimes. In fact, some loss of utero-vaginal support occurs in most adult women. POP is the leading indication for hysterectomy in postmenopausal women and accounts for 15-18% of procedures in all age groups [Kesharvarz H, Hillis S D, Kieke B A, Marchbanks P A. Hysterectomy surveillance—United States 1994-1999. *MMWR Surveill Summ* 2002; 51 (SS05):1-8]. Overall, 1 in 10 women will undergo surgery to treat pelvic floor support conditions in the course of their lifetime. This number is projected to significantly increase with the anticipated growth of the aging population in the United States. Beyond the physical impact of POP, women with progressing pelvic organ prolapse score poorer on both general and condition-specific quality-of-life scales [Jelovsek J E, Barber M D. Women seeking treatment for advanced pelvic organ prolapse have decreased body image and quality of life. *Am J Obstet Gynecol* 2006; 194: 1455-1461]. In addition, about one third of sexually active women with POP report that their condition interferes with sexual function [Barber M D, Visco A G, Wyman, et al. Sexual function in women with urinary incontinence and pelvic organ prolapse. *Obstet Gynecol* 2002; 99:281-289].

Women with symptomatic POP who fail or decline conservative management, including pessary use and physical therapy treatment, are candidates for reconstructive surgery. The overall goal for prolapse surgery is to give the most functional repair, while preventing recurrence of the condition and minimizing complications incurred by these repairs. Recurrence is one of the barriers in surgical correction most frustrating to both the surgeon and patient. Failure rates as high as 20-40% have been cited after surgical repair, with over 50% occurring within the first three years [Clemons J L, Myers D L, Aguilar V C, Arya L A. Vaginal paravaginal repair with an AlloDerm graft. *Am J Obstet Gynecol* 2003; 189(6): 1612-1618]. Since many patients with POP have inherently deficient or defective connective tissue, to minimize recurrence of POP many reconstructive surgeons have turned to the use of adjuvant materials for vaginal support. Such materials may include synthetic, allogenic, xenogenic or autologous grafts [Bako A, Dhar R. Review of synthetic mesh-related complications in pelvic floor reconstructive surgery. *Int Urogynecol J Pelvic Floor Dysfunct* 2009; 20(1):103-111]. Currently, at least 10 synthetic materials are available for vaginal use [Sung V W, Rogers R G, Schaffer J I, et al. Graft Use in Transvaginal Pelvic Organ Prolapse Repair: A Systematic Review. *Obstet Gynecol* 2008; 112(5):1131-1142]. Unfortunately, none of the currently available graft materials is ideal for restoration of both optimal support and functionality of the vaginal walls.

When determining the etiology of POP and delineating risk factors for POP, parity has the strongest association with risk of requiring surgery for POP. Pregnancy and childbirth have a tremendous impact on women's vaginal connective tissue, nerves and muscles support within the pelvis due to prolonged pressure, straining and distention forces that are placed on the pelvic tissues. Traumatic changes of the pelvic floor are encountered during childbirth including avulsion of muscle from the supporting bony structure of the pelvis, damage to vaginal support ligaments and muscle atrophy after pelvic nerve damage. Pelvic floor dysfunction, in the form of pelvic floor prolapse (including cystocele, rectocele, enterocele and uterine prolapse) and urinary and fecal incontinence are considered inevitable sequelae for some women who experience injuries during childbirth. Compared with nulliparous women, women with one child were 4 times more likely (and those with two children were 8.4 times more likely) to develop pelvic organ prolapse requiring hospital admission and surgical intervention. With the burgeoning elderly population, the latent injuries caused in childbirth will affect more and more women later in life. Although surgery for pelvic organ prolapse is effective in restoring anatomy, functional outcomes have not been as satisfactory and there are many questions regarding underlying biomechanical properties of the pelvis that are currently poorly defined to guide optimal repair.

Pelvic floor organs and support structures are elements of a biomechanical system providing critically important set of physiological processes. Despite the obvious fact that POP and childbirth damages are caused by structural failures, only recently researchers have begun to conduct a biomechanical analysis of the mechanisms of normal pelvic organ support and failure.

A critical review of published data on the urogynecologic aspects of female sexual dysfunction demonstrates a lack of standardized instruments for assessing biomechanical conditions of the pelvic floor. There is a need in 3-D imaging of vagina and its surrounding structures and reproducible measurements of vaginal tissue elasticity in-vivo because the tissue elasticity, as a capability to hold load and reversely undergoing to elongation, is the primary mechanical characteristic.

The high incidence of POP, childbirth damages and the rate of reconstructive surgery dictate the need for new effective methods for assessment of pelvic organ conditions after reconstructive surgery or other interventional procedures in women. Elasticity imaging of the vagina after reconstructive surgery may allow to quantitatively characterize the effectiveness of the surgical approach and behavior of materials used for vaginal support in-vivo.

Elasticity Imaging and Assessment of Soft Human Tissues

In the last decade, a new modality for tissue characterization has emerged termed Elasticity imaging or Elastography. Elasticity imaging allows visualization and assessment of mechanical properties of soft tissue. Mechanical properties of tissues, i.e. elastic modulus and viscosity, are highly sensitive to tissue structural changes accompanying various physiological and pathological processes. A change in Young's modulus of tissue during the development of pathological processes could reach hundreds and even thousands of percent (A. P. Sarvazyan. "Elastic properties of soft tissue", In: *Handbook of Elastic Properties of Solids, Liquids and Gases*, Volume III, Chapter 5, eds. Levy, Bass and Stern, Academic Press, 2001, pp. 107-127.). Elasticity imaging is based on generating a stress in the tissue using various static or dynamic means and then measuring resulting strain (displacements in volume) with the use of ultrasound or magnetic resonance imaging. Tactile imaging yields a tissue elasticity map similar to other elastographic techniques. At the same time, tactile imaging, unlike strain imaging, uses stress or pressure data on the surface of tissue under applied load. It mimics manual palpation, because a tactile imaging probe with a pressure sensor array mounted on its face acts similarly to a human finger during a clinical examination by compressing soft tissue with the probe and detecting resulting changes as a surface pressure pattern.

SUMMARY OF THE INVENTION

The object of the present invention is to overcome the drawbacks of the prior art and provide methods for quantitative and reproducible assessment of pelvic organ conditions affecting the vagina, including methods for estimating a risk of pelvic organ prolapse development.

Another object of the invention is to provide methods for characterizing traumatic conditions of pelvic floor structures after childbirth.

A further yet object of the invention is to provide methods for post-operative assessment of pelvic floor conditions.

The present invention involves tactile imaging and assessing tissue conditions affecting a vagina. In general, the present invention achieves this by obtaining pressure patterns and respective coordinates forming together a tactile image of the vagina and then calculating tissue elasticity and anatomy of vaginal structures therefrom.

In embodiments, methods for assessment of pelvic organ conditions affecting a vagina such as a risk of pelvic organ prolapse development may include the following steps:
(a) conducting examination of vagina by deforming vagina along an anterior vaginal wall and along a posterior vaginal wall using a transvaginal probe;
(b) obtaining pressure patterns and coordinates corresponding thereto for portions of vagina examined with the transvaginal probe;
(c) calculating at least one or both anterior elasticity modulus profile and posterior elasticity modulus profile, these elasticity modulus profiles being defined by at least two or more locations spaced apart in the respective portion of vagina examined with the transvaginal probe;
(d) calculating at least two or more distances between the anterior vaginal wall and the posterior vaginal wall along the vagina which cumulatively define a spacing profile of the vagina; and
(e) estimating a risk of pelvic organ prolapse development by comparing at least one elasticity modulus profile at the two locations against respective predetermined elasticity modulus thresholds for the same two locations as well as by comparing the spacing profile against respective predetermined distance thresholds.

In embodiments, a similar approach may be taken for assessment of other conditions affecting vagina, such as extent of pelvic support tissue impairment or damage after childbirth or an improvement after an interventional procedure such as surgery for example. Measured elasticity and geometrical parameters such as spacing profiles may be compared to predetermined normal values obtained for a plurality of patients with known clinical history or may be compared for each patient individually using results of previous examinations.

The details of embodiments of the invention are set forth in the accompanying drawings and the description below. Other features, objects, and advantages of the invention will be apparent from the description, drawings and from the claims.

BRIEF DESCRIPTION OF DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF PREFERRED EMBODIMENTS OF THE INVENTION

Figure 1:
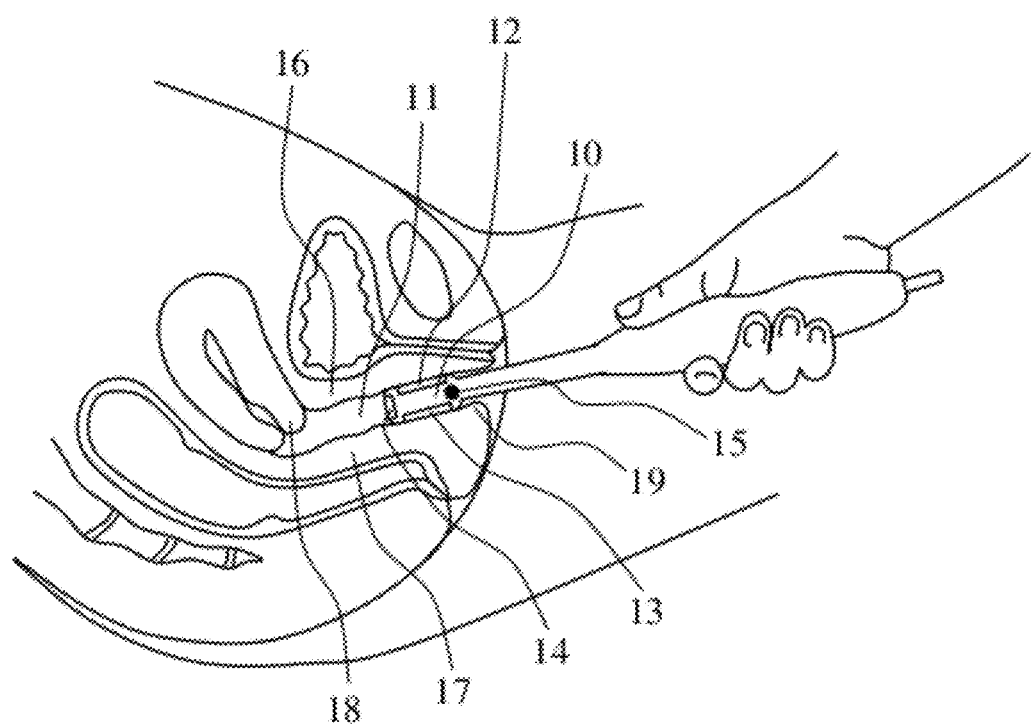
FIG. 1 illustrates a procedure of examining the vagina with a transvaginal probe.

The following description sets forth various examples along with specific details to provide a thorough understanding of claimed subject matter. It will be understood by those skilled in the art, however that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

In embodiments, methods for the assessment of pelvic organ conditions affecting the vagina employs a deformation of vaginal walls by manually operated transvaginal probe with incorporated pressure sensor arrays and motion tracking sensor. A number of pressure sensor coordinates in a coordinate system adapted for women pelvic floor together with corresponding pressure sensor signals are used to generate 3-D tactile images of the vagina. The tissue elasticity, such as for example represented by Young's modulus (E), may be calculated from spatial gradients obtained from a 3-D tactile image in the region of interest. Such elasticity modulus may be calculated in one spot or along a specified line forming an elasticity modulus profile. This approach was validated with multiple pelvic floor models built with two-component silicone having known predetermined elasticity distribution. Reproducibility of elasticity measurements with resolution better than 7% and accuracy within 20% for the tissue elasticity range between 2 kPa and 50 kPa was established after operators passed through a training program using pelvic floor models. In comparison with this broad range of elasticity, a capacity of human finger to scale the magnitude of softness of objects is substantially lower (Friedman R M, Hester K D, Green B G, LaMotte R H. Magnitude estimation of softness. Exp Brain Res 2008; 191:133-142.). This points out to a substantial advantage of using the methods of the invention in place of manual examination.

Referring now to FIG. 1, a procedure of a vaginal examination is illustrated. The examination may be performed on patient in a standard position suitable for physical examination of the vagina in a gynecologic office. During examination, the transvaginal probe 10 may be protected by a disposable elastic sheath covered with a lubricant. The transvaginal probe 10 may be placed into vagina 11 and used to deform the vaginal wall by applying a pressure load thereto. In embodiments, an exemplary examination technique includes sequential compressions of the posterior vaginal wall 17 by the probe 10 from the proximal to distal part of the vagina to collect the data along the posterior vaginal wall, allowing visualization of the posterior part of vagina in real time and calculation of an elasticity modulus profile along the examined posterior vaginal wall. Turning the probe and using the same technique, an operator may receive vaginal tactile images and elasticity modulus profiles along the examined anterior vaginal wall 16, as well as left and right sides of the vagina (not shown). Tactile imaging data coming from the transvaginal probe may be observed in three orthogonal projections representing examined parts of the vagina. A rotational motion and sliding motion of the probe 10 while exerting a load to the vaginal wall may also be used during the examination to provide a circumferential vaginal image.

Other examination techniques are also applicable for the purposes of the invention. For example, during the examination procedure, the transvaginal probe 10 may be moved along the vaginal axis without applying pressure to vaginal walls so as to record surface pressure at rest for anterior vaginal wall 16 and posterior vaginal wall 17. Also, the transvaginal probe 10 may be used for detecting muscle strength under a vaginal muscular contraction when a patient is instructed to contract appropriate vaginal muscles. The probe 10 may further be moved from hymen 19 to cervix 18 while applying pressure circumferentially to vaginal walls. An average pressure applied to vaginal wall may be in the range from about 1 kPa to about 12 kPa. The examination procedure may be performed once or may be repeated several times at one or more selected locations. In embodiments, additional passes of the probe over one or more locations along the vaginal walls may be conducted with increasing levels of the pressure, for example up to 20 kPa. Obtained data may be stored in a digital format allowing a review of one, two, or three orthogonal cross-sections selected for tactile image of vagina. Tactile images of vagina may be used for calculating elasticity modulus at specified locations or along selected lines and geometrical features. In embodiments, a spacing profile may for example be calculated as a set of distances between anterior and posterior along the vagina in at least two or more such locations.

The transvaginal probe 10 includes one or multiple pressure sensors forming one or multiple pressure sensor arrays configured for contacting vaginal walls and cervix. As shown in FIG. 1, sensor arrays 12 and 13 may be configured for a contact with opposing vaginal walls, e.g. anterior wall 16 and posterior wall 17, as well as a left side and a right side of vagina 11. Pressure sensor array 14 may be configured for a contact with cervix 18. The pressure sensor arrays may be assembled as two-dimensional sensor arrays on the part of the surface of the probe 10 adapted for contacting the vaginal tissue. The pressure-sensitive surface of the probe 10 configured for contacting the vaginal wall may have a rounded shape with a radius of curvature of about 15 mm. The pressure-sensitive surface of the pressure sensor array 14 may be flat. The motion tracking sensor 15 may be configured to record at least one or more of the three coordinates (X, Y, Z) and/or three angles (Elevation, Rotation, Azimuth) of the transvaginal probe 10. Recording coordinates and angles allows calculating coordinates of all pressure sensors of the probe 10 in a coordinate system tied to pelvic floor bony framework. An electronic unit for data acquisition may be configured to record the pressure array readings and the motion sensor readings, so that in combination, the sensor coordinates and sensor pressure data are recorded at the same time and paired together for placing into 3-D tactile image.

Figure 2:
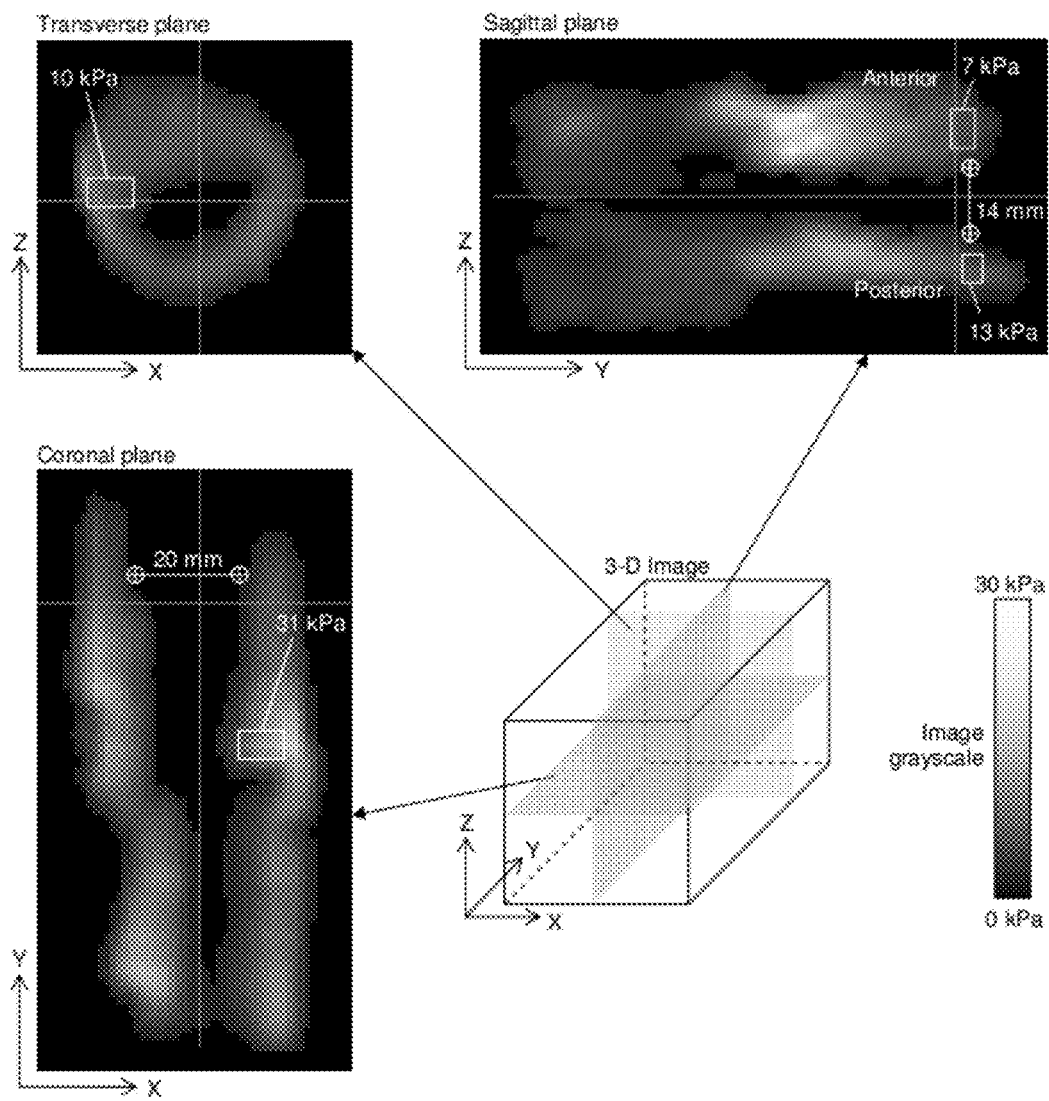
FIG. 2 shows an example of transverse, sagittal and coronal cross-sections of a 3-D tactile image of a normal vagina.

The pressure pattern on the surface of the vagina wall while deformed by the probe reveals not only elasticity conditions of vaginal wall itself, but an elasticity distribution of underlying structures: higher applied pressure reveals deeper structures surrounding vagina. The pressure patterns on the surface of vaginal walls together with tissue displacement caused by deformation from the probe may be considered as documentation of the current elasticity state of the vaginal walls and surrounding support structures. All acquired pressure patterns form together a 3-D tactile image. The 3-D tactile image of the vagina may be composed using a spatial scalar mapping of the pressure patterns acquired at the vaginal wall under deformation. The spatial mapping technique involves acquisition of probe motion tracking data, which may be transformed into spatial coordinates of each pressure sensor at the contact surface of the vaginal wall where the pressure signals were acquired during in the course of vaginal wall deformation. One practical way to observe a 3-D tactile image of vagina may be to represent it by three orthogonal cross-sections of the vagina as shown in FIG. 2. The primary regions of interest may be the anterior and posterior parts of the vagina, which are represented on the sigittal cross-section (see Sigittal plane in FIG. 2). Circumferential vaginal structures may be better observed in the transverse cross-section (see Transverse plane in FIG. 2). Left and right side support structures may be visualized in coronal cross-section (see Coronal plane in FIG. 2). Calculated tissue elasticity and geometrical measures may be projected on the respective cross-section of the 3-D tactile image to assist in visual interpretation of the examination results and comparison with reference data. Reference data may include prior measurements for the same patient or normal elasticity distributions and normal anatomical sizes obtained for a plurality of patients with known clinical status. Clinical examples of vaginal tactile images are presented in FIG. 2 and FIG. 3.

Tissue elasticity measures such as Young's modulus (E) may be calculated using a number of approaches, including:
1. comparing spatial gradients in 3-D tactile images of the vagina with the spatial gradients in 3-D tactile images for tissue models of the vagina. Such models may be prequalified to have known distribution of Young's moduli,
2. analyzing load curve for the probe during vaginal wall deformation applying a preexisting tissue deformation model,
3. using mechanical inverse problem solution applied to 3-D tactile image.

All three approaches require selection of a volume for averaging pressure gradients around the specified location where the tissue elasticity is to be calculated. Typical volume appropriate for that purpose may be in the range of 50-100 $mm^3$. The first calculating method from the listed above was used in exemplary results for tissue elasticity presented below.

FIG. 2 shows exemplary transverse, sagittal and coronal cross-sections of a 3-D tactile image of vagina for a patient with known normal pelvic floor conditions examined with the transvaginal probe. The tactile image of the vagina is presented in the units of pressure (kPa) according to specified grayscale map. 3-D tactile images of the vagina may have also color-scale map, such as the jet map. In embodiments, an operator using touchscreen capabilities of software interface may select geometrical features inside shown cross-sections to be measured, displayed and recorded in a computer-generated examination report. Selected geometrical features may include spacing between anterior and posterior walls, between left and right vaginal walls, distance between any two selected points or size of the specified zone. The operator may also select specific sites for calculation of tissue elasticity features, such as elastic modules, e.g. Young's modulus. Characteristic anatomical measures may be placed in the images and tissue elasticity values (Young's moduli) may be calculated for different sites. Comparison of different locations demonstrates the distribution of tissue elasticity. The sigittal and transverse tactile image cross-sections in FIG. 2 demonstrate strong anterior and posterior vaginal support with anterior-posterior spacing at distal part of about 14 mm. Young's modulus (E) was calculated for areas specified by a rectangular: $E=7$ kPa at distal anterior and $E=13$ kPa at distal posterior sections of vagina respectively. Right side of vaginal distal part demonstrated $E=10$ kPa (see Transverse plane in FIG. 2).

Figure 3:
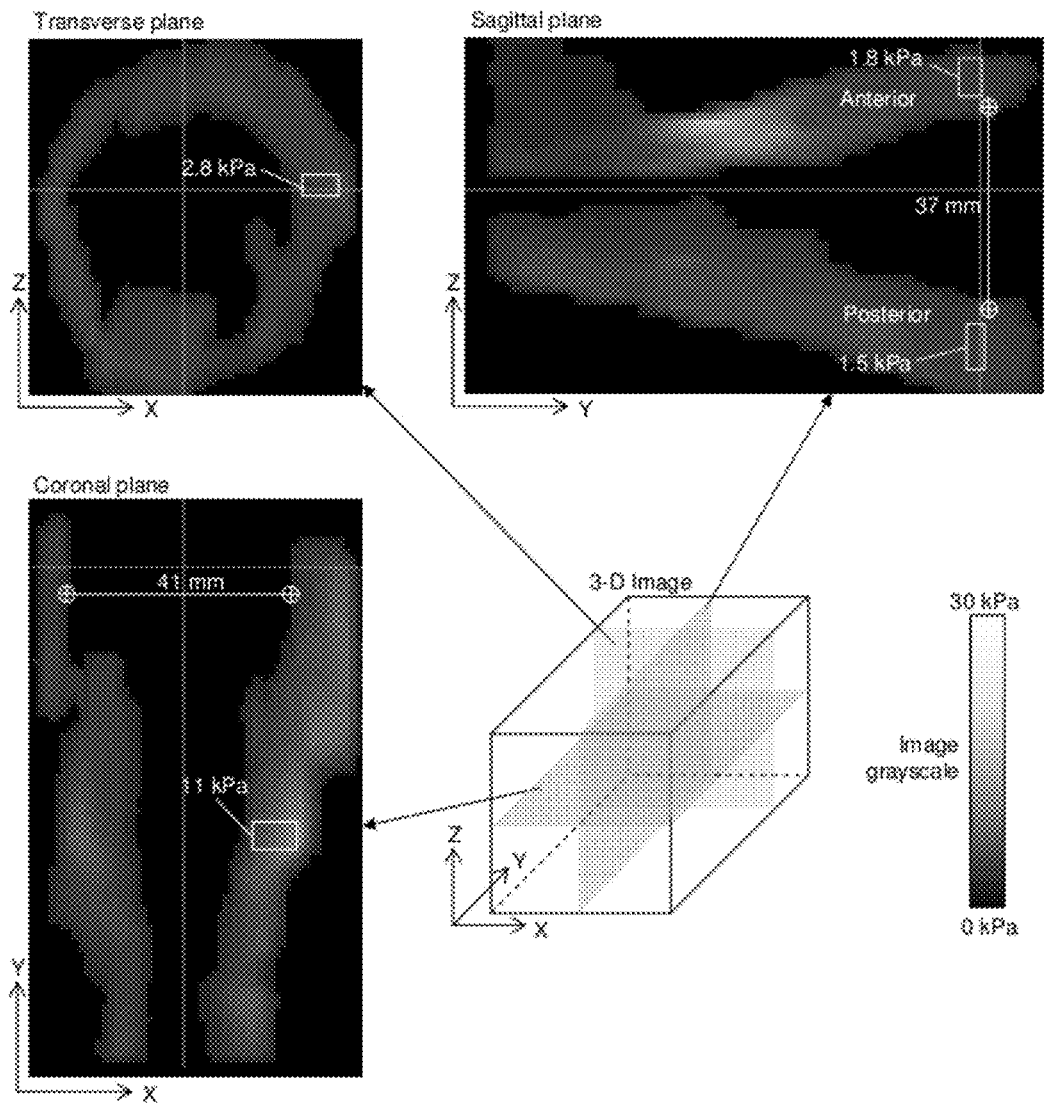
FIG. 3 shows an example of transverse, sagittal and coronal cross-sections of a 3-D tactile image for a vagina with confirmed pelvic organ prolapse.

FIG. 3 presents exemplary three orthogonal cross-sections of 3-D tactile image for a patient having a prolapse condition confirmed by physical examination. Significant difference can be observed in tissue elasticity and anatomy relatively the normal conditions shown in FIG. 2. In this clinical case, elasticity modulus was determined as $E=1.8$ kPa at distal anterior and $E=1.5$ kPa at distal posterior sections respectively. Left side of vaginal distal part demonstrated $E=2.8$ kPa (Transverse plane in FIG. 3). The anterior-posterior spacing at distal part of vagina was measured as 37 mm (Sagittal plane in FIG. 3).

Figure 4A:
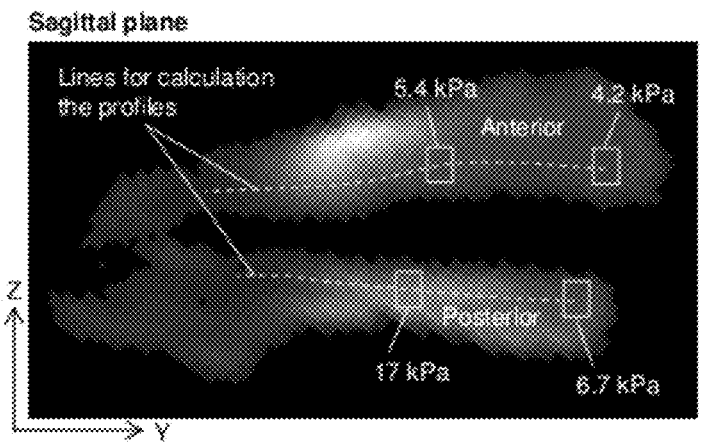
FIG. 4 shows an example of calculated elasticity modulus profiles for the anterior and posterior vaginal walls.
Figure 4B:
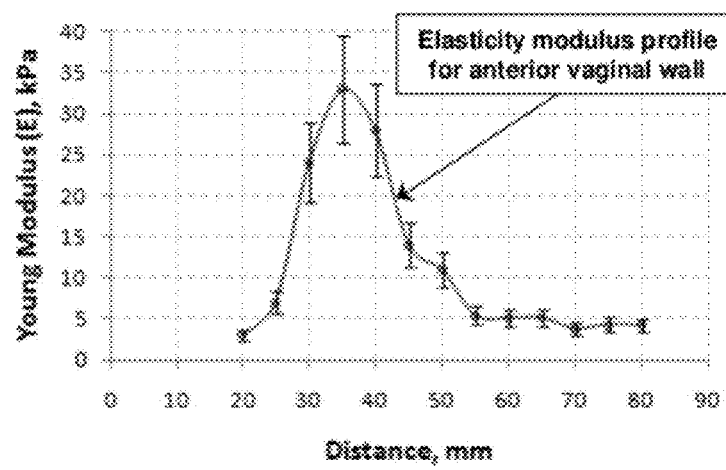
Figure 4C:
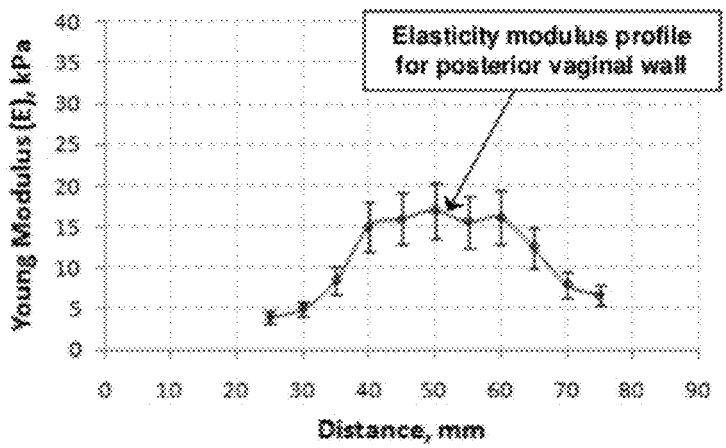

FIG. 4 is an illustration of calculating elasticity modulus profiles for the anterior and posterior vaginal walls. The sagittal cross-section of 3-D tactile image of a patient is presented in FIG. 4A. The white rectangles in FIG. 4A denote cross-sections with an average size of 5 mm×4 mm×5 mm used for a tactile gradient calculation. The tactile gradient may be calculated in the direction orthogonal to the vaginal wall boundary defined at the constant pressure level of about 1 kPa. Based on experimentation with pelvic floor models built with known Young's modulus distribution of elastic silicone, empirical equations may be derived for transforming the tactile gradient value into Young's modulus. Moving the averaging volume along a predetermined line such as the dashed lines in FIG. 4A and calculating Young's modulus along the same line allows building of the elasticity modulus profile for the anterior vaginal wall (FIG. 4B) and posterior vaginal wall (FIG. 4C). A 5 mm step may be used along the line for the elasticity modulus profile calculation. The line for elasticity profile calculation may be selected along any part of 3-D tactile image of the vagina, e.g. along the left and right vaginal walls. For characterization of elasticity conditions of the vagina and its support structures, a set of locations and threshold values of elasticity modulus for these locations may be introduced, e.g. for middle anterior, middle posterior, distal anterior and distal posterior sections of vagina.

Figure 5A:
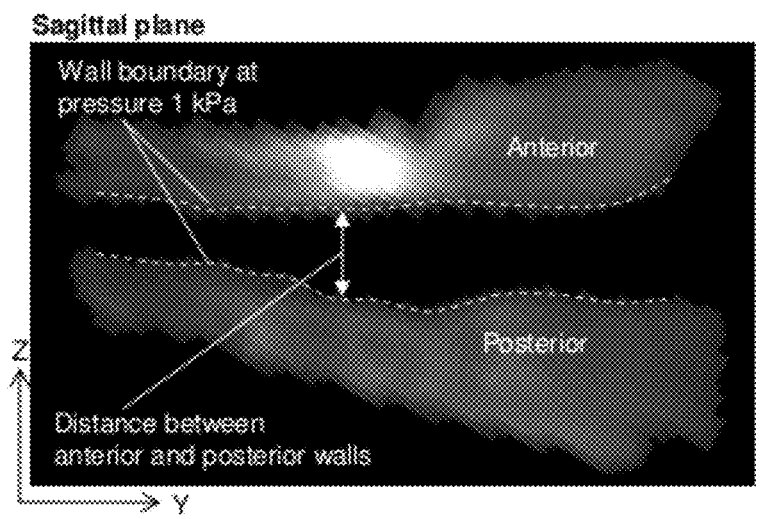
FIG. 5 shows an example of calculated spacing profile for the anterior-posterior vaginal walls.
Figure 5B:
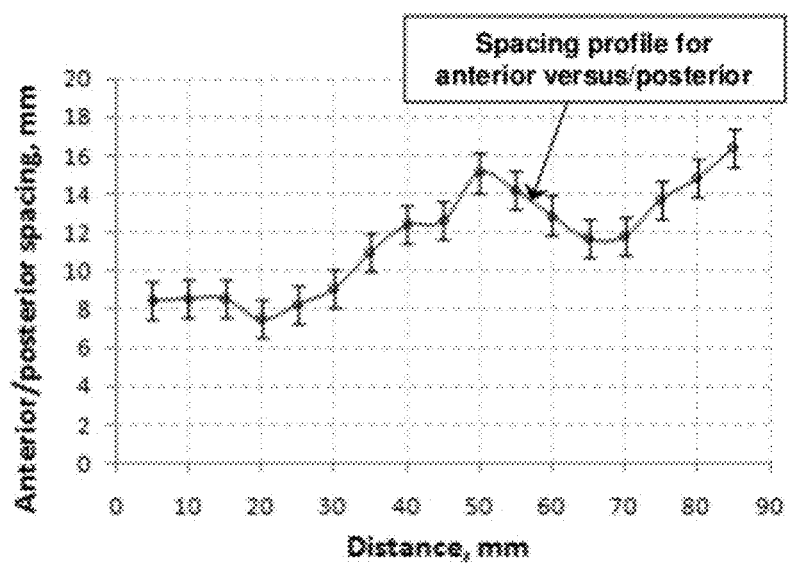

FIG. 5 is an exemplary illustration of calculating spacing profile for the anterior-posterior vaginal walls. The sagittal cross-section of 3-D tactile image of a patient is presented in FIG. 5A. The dashed lines along the anterior and posterior vaginal walls are iso-lines corresponding to a constant deformation pressure of 1 kPa; these lines define the boundaries of the vaginal walls at rest. The distances between the anterior and posterior walls boundaries, measured in generally orthogonal direction to the vaginal axis, define the spacing profile between the walls. At least two such distances are needed to establish a spacing profile. Greater number of distances improves the accuracy of the spacing profile. In embodiments, moving with a certain step (such as 5 mm) the location along the vaginal axis where the anterior-posterior distance is calculated allows building an anterior-posterior spacing profile (see FIG. 5B). The spacing profile may also be calculated for the left-right sides of the vagina. For characterization of anatomical conditions of the vagina and its support structures, a set of locations and spacing threshold values for these locations may be introduced, e.g. for proximal, middle and distal sections of vagina.

Figure 6:
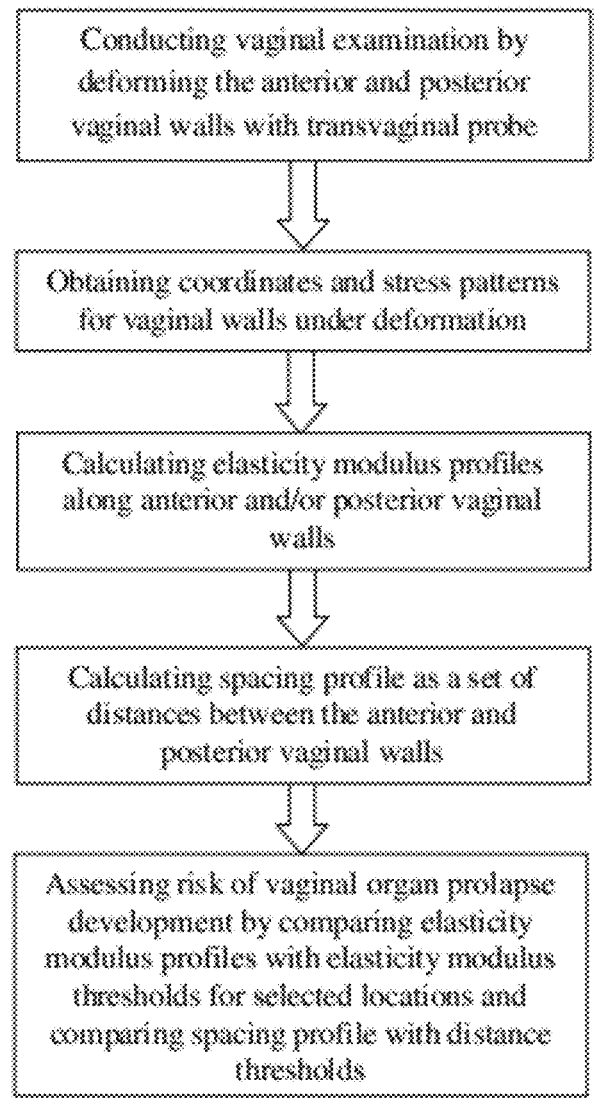
FIG. 6 is a flow chart illustrating a method for assessment of pelvic organ conditions affecting the vagina which includes the step of estimating a risk of vaginal organ prolapse development.

FIG. 6 is a flow chart illustrating one method for assessment of pelvic organ conditions affecting the vagina, in particular assessing a risk of vaginal organ prolapse development. The transvaginal probe of the invention may be used to assess the risk of development of the pelvic organ prolapse. The method of the invention is based on the notion that elasticity of the pelvic floor tissues starts to change well before the clinically-evident prolapse can be diagnosed. Early warning of the impending prolapse can therefore be obtained by recording the tactile image of the vaginal tissues and detecting the change in elasticity as compared to a predefined normal threshold. Knowing the degree of deviation of the measured values from the threshold may allow estimating a risk of vaginal organ prolapse development and may allow predicting a timeframe for its development.

In embodiments, methods for assessment of pelvic organ conditions affecting a vagina such as a risk of pelvic organ prolapse development may include the following steps:
(a) conducting examination of vagina by deforming vagina along an anterior vaginal wall and along a posterior vaginal wall using a transvaginal probe as described above;
(b) obtaining pressure patterns and coordinates corresponding thereto for portions of vagina examined with the transvaginal probe, a tactile image of the vagina may then be generated;
(c) calculating using the pressure patterns and coordinates at least one or both anterior elasticity modulus profile and posterior elasticity modulus profile, these elasticity modulus profiles being defined by at least two or more locations spaced apart in the respective portion of vagina examined with the transvaginal probe;
(d) calculating at least two or more distances between the anterior vaginal wall and the posterior vaginal wall along the vagina which cumulatively define a spacing profile of the vagina; and
(e) estimating a risk of POP development by comparing at least one elasticity modulus profile at the two or more locations against respective predetermined elasticity modulus thresholds for the same locations as well as by comparing the spacing profile against respective predetermined distance thresholds.

The values of thresholds may be defined from clinical data for a plurality of patients, in particular, for patients with known clinical diagnosis established by different modalities. The locations for comparing elasticity modulus may be selected to include distal anterior, distal posterior, middle anterior and middle posterior sections of vagina. These locations are known to closely correspond with the pelvic floor support structure. The locations for comparing distances between the anterior and posterior vaginal walls may be selected to include proximal, middle and distal sections of vagina. In embodiments, the risk of POP development may be designated as elevated if the measured elasticity falls below the following elasticity modulus thresholds 4 kPa for the distal anterior, 3.5 kPa for the distal posterior, 8 kPa for the middle anterior and 6 kPa, for the middle posterior sections respectively. The step of calculating a spacing profile may further include calculating vaginal wall coordinates along the vagina at the constant pressure level of about 1 kPa so as to establish physical locations (boundaries) of the vaginal walls at rest. In embodiments, comparison of spacing profile may be done against the distance thresholds of about 15 mm for middle section and about 25 mm for distal section of the vagina respectively. Elevated risk of POP development is detected if the spacing profile exceeds these thresholds.

In embodiments, the step of estimating the risk of POP development may also include an adjustment based on at least one or more patient-specific factors. Such patient-specific factors may include patient's age, history of childbirth, history of chronic straining to empty bowel or bladder, status of menopause, obesity, history of prior hysterectomy, history of prior pelvic surgery, history of strenuous activity, smoking status, and alcohol use status.

Figure 7:
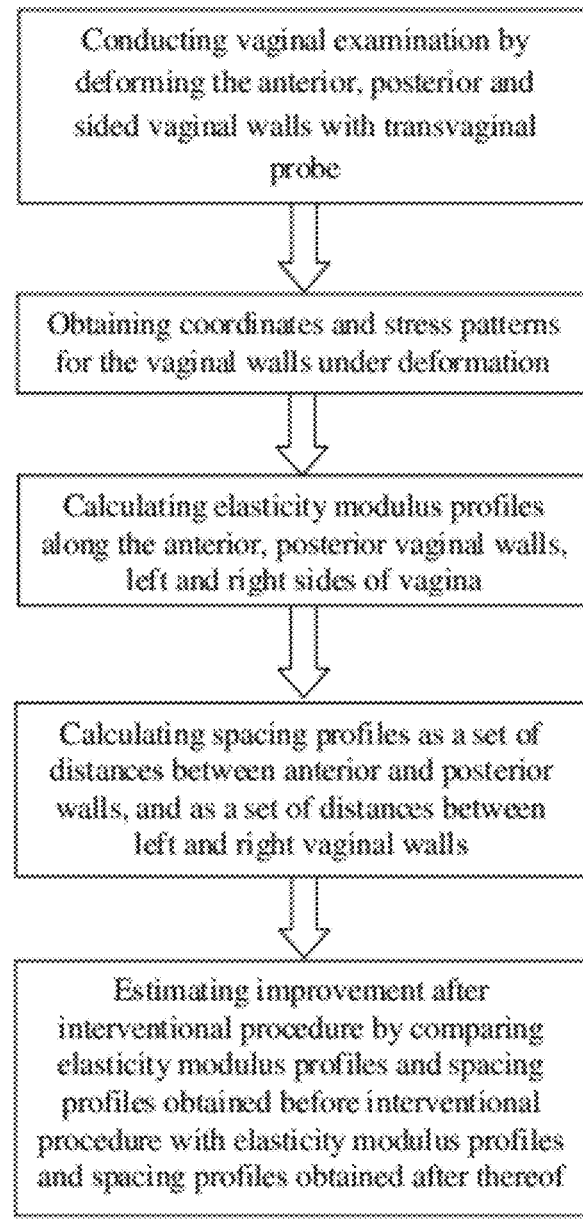
FIG. 7 is a flow chart illustrating a method for assessment of pelvic organ conditions affecting the vagina which includes the step of estimating traumatic damage after childbirth.

FIG. 7 is a flow chart illustrating a method for assessment of pelvic organ conditions affecting the vagina, in particular estimating an extent of pelvic support tissue impairment or damage after childbirth. The transvaginal probe of the invention may be used to estimate the traumatic damage. The method is based on a notion that elasticity of the pelvic floor tissues is a good predictor of vaginal tissue deviations from normal conditions including disruptions of support muscles, fascia tissue and ligaments. Knowledge of the degree of tissue damage, which is characterized by elasticity deviation, as well as damage zone size and location, may lead to an effective treatment or an intervention procedure.

In embodiments, methods for assessment of pelvic organ conditions affecting a vagina may include the following steps:
(a) conducting examination by deforming the vagina along an anterior vaginal wall, along a posterior vaginal wall, along a left side of vagina and along a right side of vagina using a transvaginal probe—as described above in greater detail;
(b) obtaining pressure patterns and coordinates corresponding thereto for portions of vagina examined with the transvaginal probe;
(c) calculating from the pressure patterns and coordinates at least one elasticity modulus profile defined by at least two or more locations spaced apart along vagina. Calculated elasticity modulus profile may include an anterior elasticity modulus profile, a posterior elasticity modulus profile, a left side elasticity modulus profile and a right side elasticity modulus profile;
(d) calculating from the same pressure patterns and coordinates at least one of an anterior-posterior spacing profile or a left-right spacing profile. The anterior-posterior spacing profile may be defined by at least two or more distances between the anterior vaginal wall and the posterior vaginal wall. The left-right spacing profile may be defined by at least two or more distances between the left side and the right side of the vagina; and
(e) estimating extent of pelvic support tissue impairment or damage after childbirth by comparing at least one or more elasticity modulus profiles against normal values such as for example corresponding elasticity modulus profile or profiles obtained for patients known to have no pelvic support tissue impairment or damage. The extent of tissue impairment or damage may be further estimated by comparing at least one or more of the calculated spacing profiles against normal values, for example against a corresponding spacing profile obtained for patients known to have no pelvic support tissue impairment or damage.

The step of estimating an extent of pelvic floor organ traumatic damage after childbirth may further include detection of a traumatic tissue damage zone and calculating a characteristic zone size of the traumatic tissue damage zone as well as elasticity modulus for the traumatic tissue damage zone using for example one of three approaches listed above.

Figure 8:
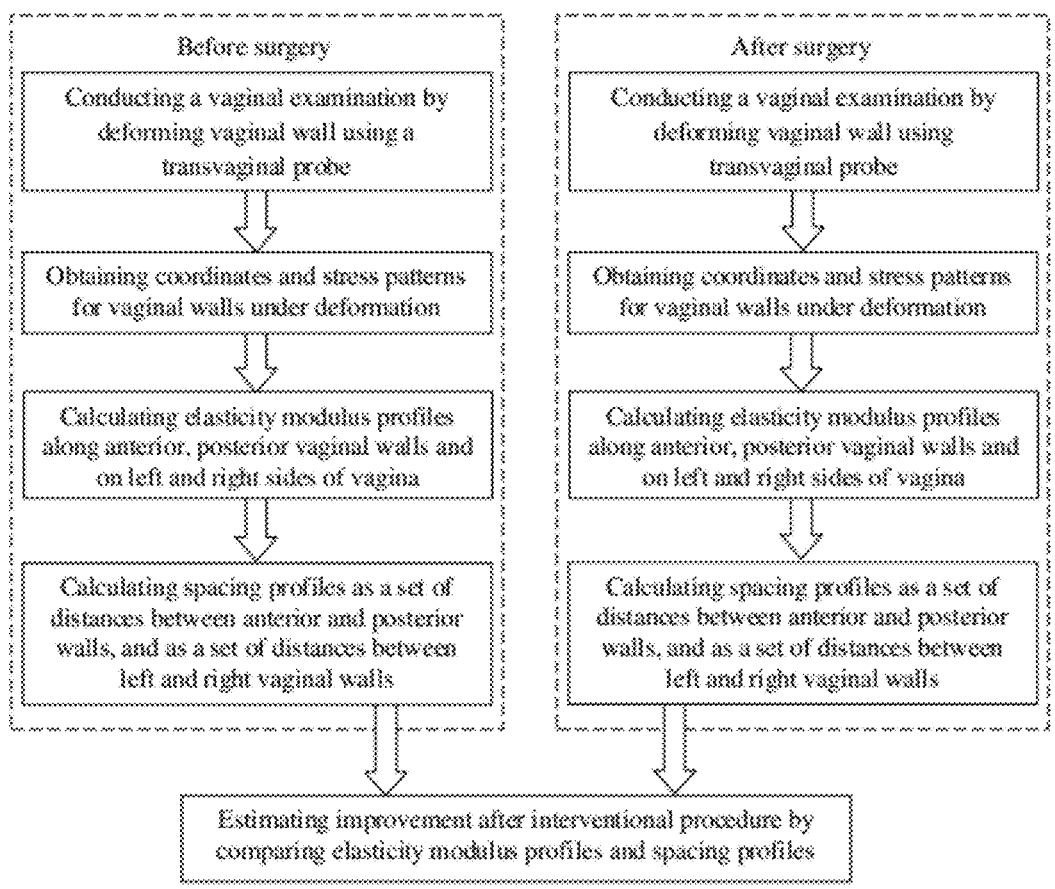
FIG. 8 is a flow chart illustrating a method for assessment of pelvic organ conditions affecting the vagina which includes the step of estimating an improvement after the interventional procedure.

FIG. 8 is a flow chart illustrating a method for assessment of pelvic organ conditions affecting the vagina, in particular estimating an improvement after an interventional procedure. Using the methods of the invention, the transvaginal probe of the invention may be used to estimate the improvement. The method of the invention is based on a notion that elasticity of the pelvic floor tissues is a good predictor of vaginal tissue conditions because pelvic organ support system including muscles, fascia tissues and ligaments is a biomechanical system responsible for vital physiological processes. One of the basic aims of pelvic floor reconstructive surgery is to correct anatomical deviations by restoring strength and elasticity of pelvic organ support structures. Knowledge of the vaginal tissue and support structure elasticity in-vivo after the surgery may allow quantitative characterization of its outcome.

The interventional procedure in which the methods of the invention are applicable may include a variety of procedures such as tissue regeneration resulting from injecting muscle cells, tissue regeneration resulting from injecting stem cells, surgical repair of the vaginal wall, surgical repair of muscle structures, surgical implantation of an artificial supporting structure, and surgical implantation of an artificial structure inside a muscle.

With regard to the elastic properties of the vaginal wall, the methods of the invention may also be useful when assessing the vaginal wall abnormalities including cancerous or pre-cancerous lesions. Vaginal and vulvar cancers are particularly difficult to detect without the application of invasive testing methods such as acetic acid, coloposcopy or direct biopsy techniques. Examination by any available means, even for screening purposes, is highly dependent on physician skill, level of suspicion for an abnormality and limitations of performing the exam. The use of methods of the invention for tissue elasticity quantification with the transvaginal probe may solve this problem because cancerous tissue is known to have increased hardness.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for assessment of pelvic organ conditions affecting a vagina, said method comprising the steps of:
   (a) conducting examination of said vagina before and after an interventional procedure by deforming said vagina along an anterior vaginal wall, along a posterior vaginal wall, along a left side of said vagina and along a right side of said vagina using a transvaginal probe;
   (b) obtaining pressure patterns and coordinates corresponding thereto for portions of vagina examined with said transvaginal probe before and after said interventional procedure;
   (c) calculating from said pressure patterns and coordinates at least one elasticity modulus profile defined by at least two locations spaced apart in said vagina, said at least one elasticity modulus profile is selected from a group consisting of anterior elasticity modulus profile, posterior elasticity modulus profile, left side elasticity modulus profile and right side elasticity modulus profile;
   (d) calculating from said pressure patterns and coordinates at least one of an anterior-posterior spacing profile or a left-right spacing profile, said anterior-posterior spacing profile is defined by at least two distances between said anterior vaginal wall and said posterior vaginal wall, said left-right spacing profile is defined by at least two distances between said left side and said right side of said vagina; and
   (e) estimating an improvement after said interventional procedure by comparing said at least one elasticity modulus profile obtained before said interventional procedure and after thereof, same improvement is further estimated by comparing said at least one spacing profile obtained before said interventional procedure and after thereof.

2. The method as in claim 1, wherein said interventional procedure is selected from a group consisting of: tissue regeneration resulting from injecting muscle cells, tissue regeneration resulting from injecting stem cells, surgical repair of the vaginal wall and surrounding support tissues, surgical repair of muscle structures, surgical implantation of an artificial supporting structure, and surgical implantation of an artificial structure inside a muscle.

3. The method as in claim 1, wherein said step (e) further including said at least one spacing profile against a predetermined threshold obtained using clinical data from patients with known clinical diagnosis.

4. The method as in claim 1, wherein said step (e) further including quantification of vaginal tissue elasticity using said at least one elasticity modulus profile, said quantification used to detect a vaginal wall abnormality in a location with increased hardness.

5. The method as in claim 4, wherein said vaginal wall abnormality is a pre-cancerous lesion or a cancerous lesion.

* * * * *